United States Patent
Shabudin

(10) Patent No.: US 11,364,342 B2
(45) Date of Patent: Jun. 21, 2022

(54) INJECTION DEVICE

(71) Applicant: Owen Mumford Limited, Oxford (GB)

(72) Inventor: Tahir Shabudin, Oxford (GB)

(73) Assignee: Owen Mumford Limited, Oxfordshire (GB)

( * ) Notice: Subject to any disclaimer, the term of this patent is extended or adjusted under 35 U.S.C. 154(b) by 263 days.

(21) Appl. No.: 16/338,214

(22) PCT Filed: Oct. 2, 2017

(86) PCT No.: PCT/GB2017/052955
§ 371 (c)(1),
(2) Date: Mar. 29, 2019

(87) PCT Pub. No.: WO2018/060744
PCT Pub. Date: Apr. 5, 2018

(65) Prior Publication Data
US 2020/0023130 A1    Jan. 23, 2020

(30) Foreign Application Priority Data
Sep. 30, 2016  (GB) ..................................... 1616709

(51) Int. Cl.
*A61M 5/20*  (2006.01)
*A61M 5/315*  (2006.01)

(52) U.S. Cl.
CPC ........ *A61M 5/2033* (2013.01); *A61M 5/3158* (2013.01); *A61M 2005/206* (2013.01); *A61M 2005/2086* (2013.01)

(58) Field of Classification Search
CPC .............. A61M 5/2033; A61M 5/3158; A61M 2005/206; A61M 2005/2086; A61M 5/20;
(Continued)

(56) References Cited

U.S. PATENT DOCUMENTS

2005/0222539 A1   10/2005   Gonzales et al.
2013/0046238 A1*  2/2013   Edhouse ........... A61M 5/31595
                                                    604/134
(Continued)

FOREIGN PATENT DOCUMENTS

AU    2016222391 A1    9/2016
CN    103533974 A      1/2014
(Continued)

OTHER PUBLICATIONS

International Search Report and Written Opinion, International Application No. PCT/GB2017/052955, dated Jan. 4, 2018, 17 pages.
(Continued)

*Primary Examiner* — Bhisma Mehta
*Assistant Examiner* — Nidah Hussain
(74) *Attorney, Agent, or Firm* — Quarles & Brady LLP

(57) ABSTRACT

An injection device for delivering a dose of medicament from a syringe (5), the injection device comprising a housing (10), a plunger (210) moveably mounted within the housing (10), an actuation mechanism (200), a trigger mechanism (40), and a plunger velocity regulator. The actuation (mechanism (100) is arranged to provide a forward biasing force to urge the plunger (210) forward in use to express a dose of medicament, and the trigger mechanism (40) is arranged to releasably hold the plunger (210) against the force of the actuation mechanism (200). The plunger velocity regulator comprises a cam surface (262) associated with the housing, and a cam member (252) associated with the plunger (210) and arranged to engage the cam surface (262) during actuation movement of the plunger (210) such that axial movement of the plunger (210) relative to the housing (10) causes relative rotational movement of the cam member (252) which limits the forward velocity of the plunger movement.
(Continued)

The plunger (210) is axially connected to the cam member (252) by a releasable coupling (300), and the plunger velocity regulator further comprises a coupling member (350) which blocks release of the releasable coupling (300) when the plunger (210) is in a rearward position and wherein forward movement of the plunger (210) moves the releasable coupling (300) out of engagement with the coupling member (350) such that the plunger (210) may disengage the cam member (252) after an initial movement of the plunger (210).

18 Claims, 6 Drawing Sheets

(58) Field of Classification Search
CPC .......... A61M 5/31501; A61M 5/31505; A61M 2005/2006; A61M 2005/2073; A61M 2005/3143; A61M 2005/31508
USPC ........................................................ 604/135
See application file for complete search history.

(56) References Cited

U.S. PATENT DOCUMENTS

| | | |
|---|---|---|
| 2013/0237921 A1 | 9/2013 | Lannan et al. |
| 2013/0317427 A1 | 11/2013 | Brereton et al. |
| 2014/0046259 A1 | 2/2014 | Reber et al. |
| 2014/0343508 A1* | 11/2014 | Hourmand .......... A61M 5/2033 604/198 |
| 2016/0008542 A1 | 1/2016 | Hirschel et al. |
| 2016/0287791 A1 | 10/2016 | Olson |

FOREIGN PATENT DOCUMENTS

| | | |
|---|---|---|
| CN | 104334217 A | 2/2015 |
| CN | 104768592 A | 7/2015 |
| CN | 105492042 A | 4/2016 |
| CN | 105828854 A | 8/2016 |
| DE | 102007030327 A1 | 1/2009 |
| EP | 2399627 A1 | 12/2011 |
| GB | 2538566 A | 11/2016 |
| WO | 2011162686 A1 | 12/2011 |
| WO | 2015138261 A1 | 9/2015 |
| WO | 2016051168 A2 | 4/2016 |
| WO | 2016189286 A1 | 12/2016 |

OTHER PUBLICATIONS

Search Report, related UK Application No. GB1616709.0, dated Mar. 3, 2017, 4 pages.
First Office Action from corresponding Chinese Patent Application No. 201780053498.X, dated Mar. 2, 2021 (15 pages) (only partial English translation available).

* cited by examiner

INJECTION DEVICE

CROSS-REFERENCE TO RELATED APPLICATIONS

This application represents the U.S. National Stage of International Application No. PCT/GB2017/052955 filed Oct. 2, 2017, which is based on, claims priority to, and incorporates herein by reference in its entirety, British Patent Application Serial No. GB 1616709.0, filed Sep. 30, 2016, and entitled, "Injection Device."

FIELD OF THE INVENTION

This invention relates to injection devices for delivering a dose of medicament from a syringe. In particular, but not exclusively the invention relates to an autoinjector type device.

BACKGROUND OF THE INVENTION

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament, such as Insulin. Such devices may be either single use "disposable" devices in which the device is typically provided with a syringe already installed, and which is not user-replaceable, or "reusable" devices which allow the user to replace the syringe when the medicament has been used.

It may be noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial stiction between the bung and syringe may resist forward movement of the piston relative to the syringe such that initially the delivery arrangement moves the syringe into the needle insertion position (whereupon further movement of the syringe is blocked and the delivery arrangement will continue to move forward thus moving the bung). A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a drive spring (for example a compression spring) which is held in an energised (or primed position) prior to release by the trigger.

Accordingly, the applicant has proposed a revised injection device in co-pending International Application PCT/GB2016/051471. The injection device includes a plunger velocity regulator which limits the forward velocity of the plunger movement for at least a portion of the actuation/delivery movement. The velocity regulator arrangement includes a cam surface (associated with one of the housing or the plunger) and a cam member (associated with the other of the plunger or the housing). Engagement of the cam surface with the cam member causes axial movement of the plunger, under the drive of the delivery mechanism, to cause relative rotational movement of the cam member and limits the forward velocity of the plunger movement. The velocity regulator may be configured to limit the speed of the plunger movement during only a limited axial portion of the plunger movement. In particular, the applicant has recognised that the Velocity regulator may be arranged to disengage after an initial movement of the plunger. For example, the velocity regulator may limit the speed during a needle insertion movement before allowing the plunger to accelerate under the full force of the delivery mechanism to be applied to the plunger during a drug delivery phase.

The applicants have now identified further modifications and/or improvement to the device of PCT/GB2016/051471.

SUMMARY OF THE INVENTION

Accordingly, the invention provides an injection device for delivering a dose of medicament from a syringe, the injection device comprising:
 a housing;
 a plunger moveably mounted within the housing;
 an actuation mechanism arranged to provide a forward biasing force to urge the plunger forward in use to express a dose of medicament;
 a trigger mechanism arranged to releaseably hold the plunger against the force of the actuation mechanism;
 wherein the injection device further comprises:
 a plunger velocity regulator comprising:
  a cam surface associated with the housing, and
  a cam member associated with the plunger and arranged to engage the cam surface during actuation movement of the plunger such that axial movement of the plunger relative to the housing causes relative rotational movement of the cam member which limits the forward velocity of the plunger movement; and wherein
 the plunger is axial connected to the cam member by a releasable coupling; and
 the plunger velocity regulator further comprises a coupling member which blocks release of the releasable coupling when the plunger is in a rearward position and wherein forward movement of the plunger in use, following release of the actuation mechanism, moves the releasable coupling out of engagement with the coupling member such that the plunger may disengage the cam member after an initial movement of the plunger.

Advantageously, embodiments of the invention do not require relative rotation of the plunger and cam member. As such, the sequencing and reliability of the release of the velocity regulator may be improved. A further advantage of embodiments of the invention is that the size of the connecting features on the plunger may be reduced in comparison to the embodiments disclosed in PCT/GB2016/051471 (for example, by removing the need for a keyed engagement between the plunger and the cam member). This may provide increased design flexibility for example if a stronger plunger is required (for example when using a high viscosity drug) or to enable the plunger to be fully or partially hollow. This may for example be useful in providing an indication arrangement (for example using a telescopic plunger arrangement).

After an initial period of actuation movement of the plunger the plunger may for example be moved forward of the coupling member.

The injection device may be an autoinjector device arranged to both provide needle insertion and drug delivery. The actuation mechanism may have a first phase of operation in which the actuation mechanism displaces a syringe relative to the housing to automate the insertion of a needle into the skin; and a second phase of operation in which the plunger is displaced relative to the syringe to cause delivery of the medicament. The coupling member may block release of the releasable coupling during the first phase of operation.

The releasable coupling may comprise interconnecting engagement features on the plunger and the cam member. A resilient portion of the cam member may be deflectable to disengage the interconnecting engagement features.

The coupling member may be configured to blocks deflection of the resilient portion of the cam member. Forward movement of the plunger may move the releasable coupling out of blocking alignment with the coupling member.

The releasable coupling may comprises a plurality of interconnecting engagement features on the plunger and/or the cam member. The resilient portion of the cam member may comprise a plurality of resilient portions.

The releasable coupling may comprise a plunger interconnecting feature comprising an annular feature (for example a groove or projection) extending around the outer surface of the plunger and a cam member interconnecting feature comprising at least one projection or recess for engaging the annular feature. The plunger may for example be provided with a localised reduced diameter section (For example a circumferential groove). By providing an annular, circumferentially aligned, feature on the plunger the axial connection between the plunger and the cam member may allow relative rotation whilst the releasable coupling is engaged.

The resilient portion of the cam member may comprise a plurality of flexible members. For example the flexible members may comprise a plurality of fingers or segments circumferentially distributed around the cam member. Each flexible member may have a cam member interconnecting feature provided thereon. For example, the flexible members may extend in a generally axial direction (for example rearwardly) from the cam member and may, for example, be provided with a recess or projection at a rearward end for releasably engaging a corresponding feature on the plunger.

The plurality of flexible members may comprise a plurality of resilient segments formed in a reduced diameter rearward portion of the cam member.

The coupling member may substantially surround the releasable coupling (when in the blocking configuration). For example the coupling member may comprise an annular collar. It will be appreciated that the plunger, cam member, releasable coupling and coupling member may be coaxially arranged.

The coupling member may extend forwardly from a rearward surface of the device, for example a surface associated with the trigger. The coupling member could be an integrally formed forwardly extending element or could be a discrete component. The trigger may, for example, include a latch surface which extends substantially transversely across the injection device. The latch surface may be arranged to engage and hold a rearward portion of the plunger. The coupling member may extend forwardly from the latch surface.

The coupling member may include a seat for a drive spring of the actuation mechanism. The seat may, for example, comprise a radial flange at a rearward end of the coupling member. With the drive spring seated on the seat the coupling member may be held captive between a rearward surface (for example the latch surface) and the drive spring (which is typically a compression spring). This may provide a convenient means for assembly when the coupling member is a discrete component.

The cam member may also be configured as an intermediate drive member of the actuation mechanism. For example, the actuation mechanism may comprise a first drive spring disposed between the cam member and the housing (or a featured fixed relative to the housing) to urge said collar forward during actuation movement. A second spring disposed between the cam member and the plunger to urge the plunger forward during activation movement. The first spring may be released upon release of the plunger by the trigger mechanism. The second spring may be released when the plunger is axial disconnected from the cam member by the releasable coupling.

The cam surface may be provided on a discrete component and fixed relative to the housing. However, in other embodiments the cam surface may be formed integrally with the housing. The cam surface may be a forwardly sloped inclined cam surface. The cam surface may be circumferentially extending. The cam surface may be a slot or groove which is engaged by a corresponding projection of the cam member. For example the cam surface may comprise an internal thread defined on an inner surface of the injection device. The internal surface may be any convenient surface which is fixed relative to the housing.

It will be appreciated that the "association" with the housing/plunger may mean that the cam member or cam surfaces is either on, or coupled to, the housing/plunger.

The velocity regulator may be configured such that the cam member and cam surface only control the velocity of the plunger during only a portion of the movement of the plunger. For example, the velocity regulator may limit the speed of the plunger for the first 15% to 20% of the total movement of the plunger required to deliver a complete dose. This portion of the movement may generally correspond to an initial portion of the movement of the plunger. However, it will be appreciated that there may be a degree of free movement of the plunger before the cam surfaces of the velocity regulator are brought into engagement (for example to allow for manufacturing tolerances within the device and/or to avoid any interference with the initial triggering of the actuation mechanism). The limited axial extent of the engagement may correspond to the axial position of the cam member during an initial movement of the plunger. In other words, the plunger velocity regulator may only be active during an initial movement of the plunger (for example a rearward portion of the plunger stroke). Such an arrangement may, for example, be provided such that the velocity regulator only limits the speed of the plunger movement during an initial movement of the plunger (which may for example be until the plunger has engaged the bung or until the syringe has reached the required insertion depth). After this period the plunger may be free to accelerate under the force of the actuation mechanism.

Embodiments of the invention may be particularly useful for use in devices in which a spring force of 30N or more is utilised.

The velocity may, for example, limit the velocity by up to 75% of the normal velocity at which the plunger would be displaced in a corresponding device without the inclusion of the regulator.

According to a further aspect of the invention there is provided, an injection device for delivering a dose of medicament from a syringe, the injection device comprising: a housing; a plunger moveably mounted within the housing; an actuation mechanism arranged to provide a forward biasing force to urge the plunger forward in use to express a dose of medicament, the actuation mechanism comprising: an intermediate drive member, a first drive spring disposed between the intermediate drive member and the housing, or a featured fixed relative to the housing, to urge said intermediate drive member forward during actuation movement, and a second spring disposed between the intermediate drive member and the plunger to urge the plunger forward during activation movement; a trigger mechanism arranged to releaseably hold the actuation mechanism when the device is in a pre-use configuration; and wherein the trigger arrangement comprises a latch which releasably engages the intermediate drive member to hold the intermediate drive member in a rearward, pre-firing, position against the force of the actuation mechanism; and the plunger is releasable coupled to the intermediate drive member such that the plunger and intermediate drive member are axially fixed when the latch is holding the intermediate drive member.

The plunger may be releasably coupled to the intermediate drive member for at least a portion of the of the actuation movement. For example the plunger and intermediate drive may be coupled for an initial stage of the actuation before decoupling to allow the plunger to move axially forwardly relative to the intermediate member (for example under the force of the second drive spring).

The injection device may further comprises a coupling member which blocks release of the releasable coupling when the plunger is in a rearward position. For example the coupling member may be substantially of the type disclosed in the above embodiments. Forward movement of the plunger may moves the releasable coupling out of engagement with the coupling member such that the plunger may disengage the cam member after an initial movement of the plunger.

Whilst the invention has been described above, it extends to any inventive combination of the features set out above or in the following description or drawings.

DESCRIPTION OF EMBODIMENTS

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use.

Axial, radial and circumferential are used herein to conveniently refer to the general directions relative to the longitudinal direction of the injection device (or components thereof). The skilled person will, however, appreciated that these terms are not intended to be narrowly interpreted (and for example, the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
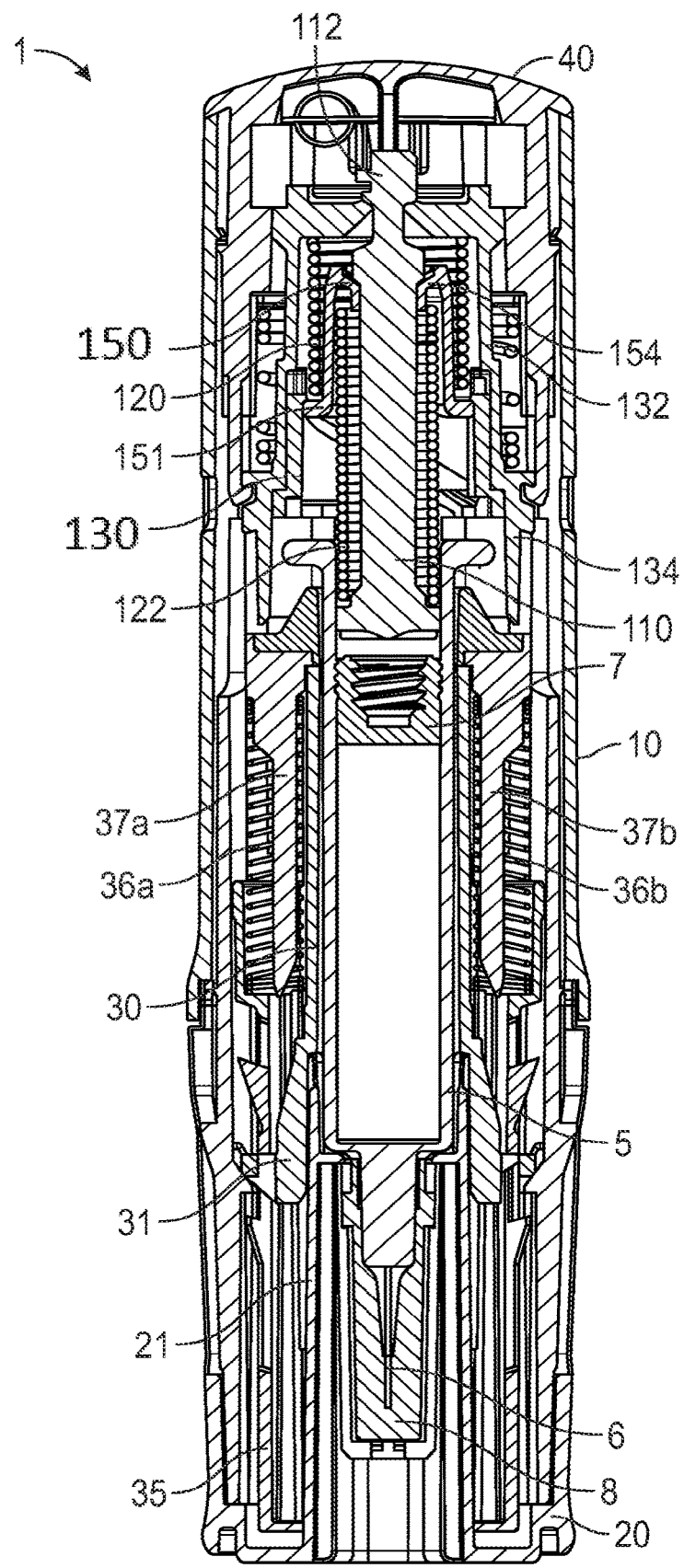
FIG. 1 shows a cross-sectional view of an autoinjection device of the type used in an embodiment of the invention.

FIG. 1 shows a cross sectional view of an autoinjector 1 as disclosed in the Applicants' earlier International Patent Application PCT/GB2016/051471. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may initially be protected (so as to remain sterile) by a removable needle shield 8. The illustrated autoinjector 1 is generally intended to be a single use device (although the skilled person will appreciate that the invention is not limited to such devices) and, therefore, the view of FIG. 1 may typically represent a fully assembled, ready to use device as provided to an end user would typically be provided (with the autoinjector 1 preassembled around the syringe 5). A cap 20 is provided which closes the forward end of the autoinjector 1 prior to use. The cap 20 may include an internal formation, comprising rearwardly extending members 21, arranged to engage the removable needle shield 8 of the syringe 5 such that removal of the cap 20 from the housing 10 during use also removes the removable needle shield 8 from the syringe 5.

The autoinjector 1 may conveniently be considered to comprise a forward subassembly in a forward portion of the housing 10 and a rearward assembly in a rearward portion of the housing 10. The two housing portions may be snap fit together during assembly. The forward subassembly may comprise the components which surround and/or are initially forward of the syringe 5. The rearward subassembly may comprise those components which are initially rearward of the syringe 5. The present invention is associated with the actuation mechanism which is in the rearward subassembly and as such the forward components may be of any convenient known arrangement. As such the forward components will be only briefly described herein.

A forward portion of the housing 10 may contain a syringe carrier 30 for movably mounting the syringe within the housing 10 to enable automatic needle penetration. It may be noted that prior to the removal of the cap 20, the rearwardly extending members 21 of the cap 20 underlie spring fingers 31 of the syringe carrier 30. This arrangement, thus prevents inward movement of the spring fingers 31 prior to removal of the cap 20 and, therefore, blocks unlatching of the syringe carrier 30 and prevents movement relative to the housing 10.

A needle shroud 35 is also provided and arranged to shroud the needle after use (when the syringe 5 and syringe carrier 30 are in a forward position) to prevent needle stick injuries. The shroud 35 is activated by a pair of side-by-side shroud springs 36a, 36b carried on respective spring guides 37a, and 37b. The present application is not limited to any arrangement of the syringe carrier 30 and/or needle shroud 35 (and some embodiments may even omit one or both of the features). As such the operation of the shroud 35 and carrier 30 is not described herein. However, it may be noted that the arrangement substantially corresponds to the arrangement of the Applicants' earlier International Patent Application PCT/GB2011/052557.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms which are arranged to provide an engagement between the trigger button 40 and the injector 1.

The rearward portion of the housing 10 also includes the actuation mechanism. The actuation mechanism includes a plunger 110 which is arranged to engage the bung 7 of the syringe 5 in use. The plunger 110 is driven forwards in use by a pair of concentric drive springs 120 and 122 (although it will be appreciated that in other embodiments a single spring may be used). An intermediate drive member 150 in the form of a substantially cylindrical member (which also functions as part of the velocity regulator as described below) is provided between the first 120 and second 122 drive springs. A latch 130 is arranged concentrically around the drive springs 120, 122, intermediate member 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the actuation mechanism is substantially as described, for example, in the applicants' earlier International Patent Applications PCT/GB2011/051950 and PCT/GB2014/052276.

As noted above, the actuation mechanism includes a latch member 130 which is fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which may initially be retained in position by the pair of arms. In a central portion of the inner surface of the rearward face of the button 40 a forwardly extending boss is provided which may act to urge the plunger 110 out of engagement with the latch member 130 during activation (in a manner such as that described in the applicants earlier patent applications referred to above).

The actuation mechanism of the autoinjector device 1 also includes a velocity regulator arranged to control or limit the initial velocity of the plunger 110 upon release of the actuation mechanism. As will be explained with reference to an embodiment of the invention below, the velocity regulator utilises cam members which travel along a cam surface which provides an inclined plane along which the cam member will travel during actuation.

In addition to carrying the cam members, the intermediate drive member 150 acts between the first compression spring 120 and second compression spring 122. Accordingly, the intermediate drive member 150 includes an external radial flange 151 at its forward end which provides a seat for the first compression spring 120 and an internal radial flange 154 at its rearward end which provides a seat for the second compression spring 122. The internal flange 154 at the rear of the intermediate drive member 150 includes an aperture through which the head 112 of the plunger extends when the actuation mechanism is in the pre-fired (or primed) condition.

As discussed above, in the embodiments disclosed in PCT/GB2016/051471 the aperture is provided with a keyed profile which interacts with a profiled cross-section of the plunger 110. The key and profiled section hold the intermediate drive member 150 and plunger 110 in engagement until they have rotated relatively by a predetermined amount.

The applicants have now recognised that in some devices this rotational engagement between the plunger and velocity control arrangement may provide limitations in the type of plunger which may be used. Furthermore, it may be desirable to provide an alternate arrangement in which the sequencing of the release is not dependent on relative rotation (since relative rotation between engaged surfaces can lead to a risk of stalling and/or hesitation during activation).

Figure 2:
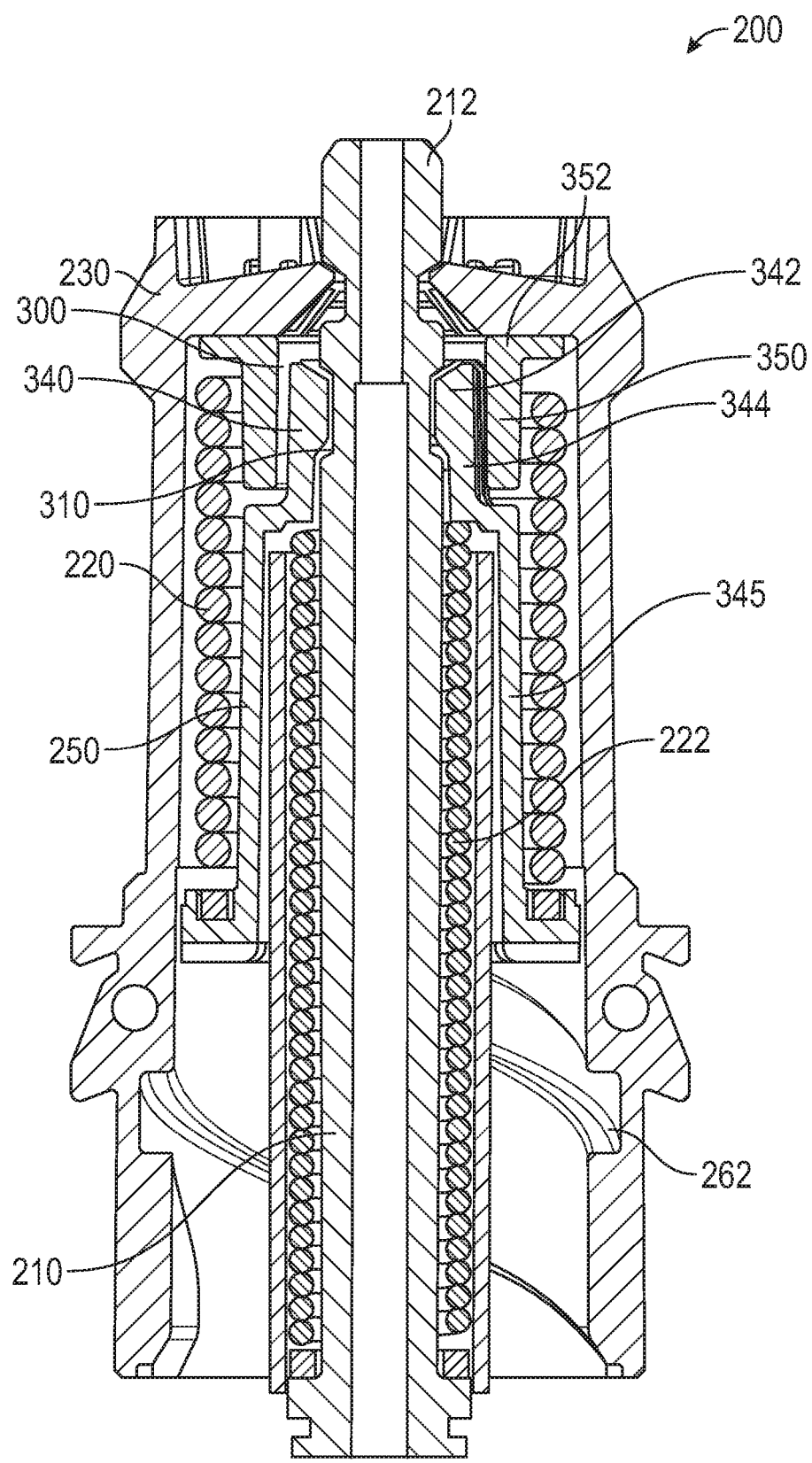
FIG. 2 shows a cross-section, partial three-dimensional view of a modified actuation mechanism including a velocity regulator in accordance with an embodiment of the invention in a pre-fired state.
Figure 3:
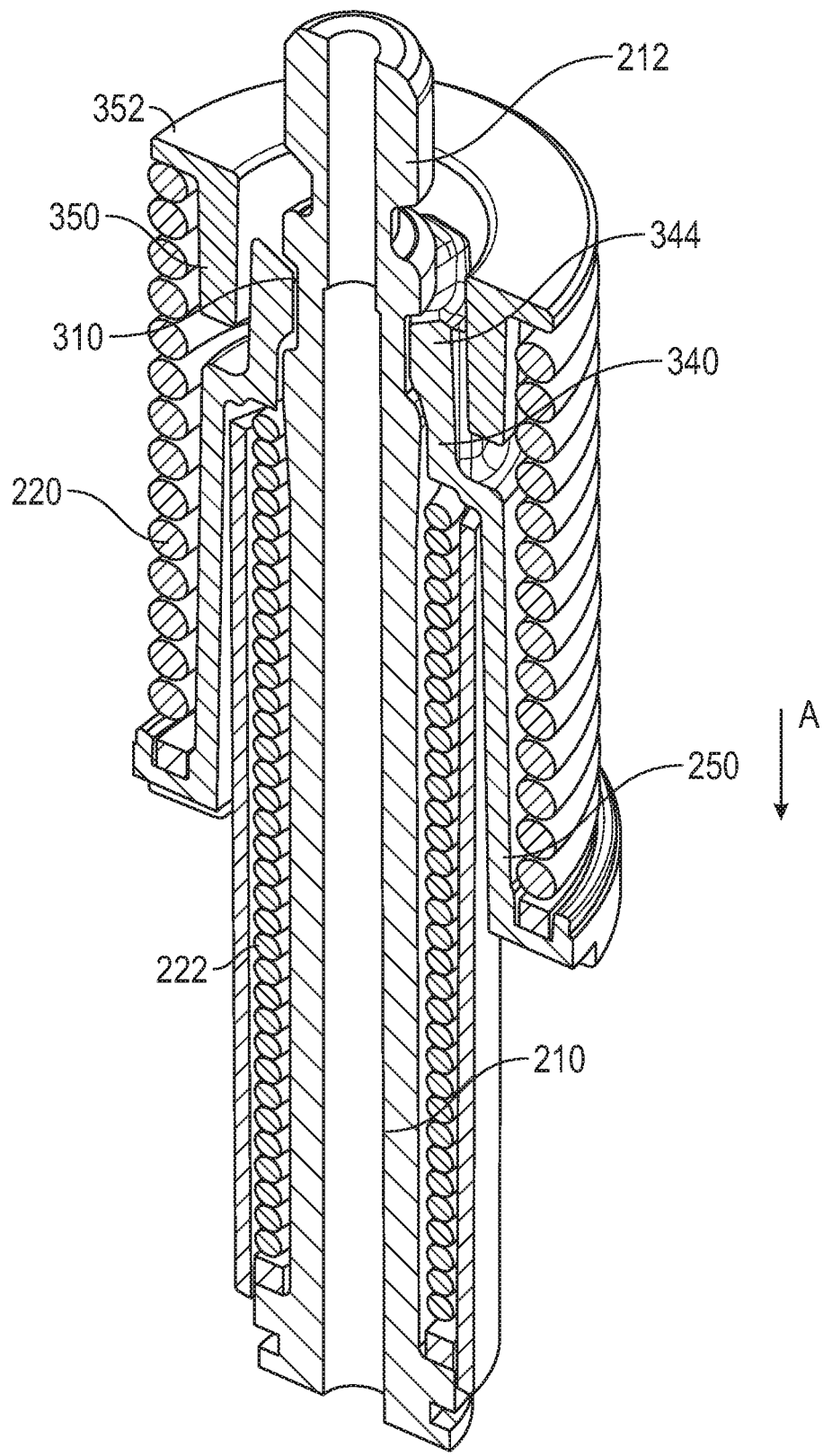
FIG. 3 shows a cross sectional side view of the actuation mechanism of FIG. 2 including a latch arrangement.

Accordingly, a modified drive arrangement 200, including a revised plunger velocity control arrangement. The skilled person will appreciate that the underlying functional arrangement of an autoinjector according to an embodiment a of the device of the invention is unchanged in comparison to that of PCT/GB2016/051471 and as such, the revisions to the actuation mechanism are shown, and described below, in isolation in FIGS. 2, 3 and 4.

In the revised actuation mechanism 200, a releasable coupling 300 is provided between the plunger 210 and the intermediate drive member 250. As in the previous arrangement, it will be noted that the intermediate drive member 250 provides multiple functions. In particular the intermediate drive member 250 is disposed between and acted upon by the two drive springs 220, 222, the intermediate drive member 250 acts as a cam member as it included cam elements 252 (best seen in FIG. 4) at a forward end and the releasable coupling 300 between the cam elements 252 and the plunger 210 is integral to the intermediate drive member 250.

For the plunger 210 releasable coupling arrangement 300 comprises a circumferentially extending groove or recess 310 formed in a rearward portion of the plunger 210, forward of the plunger head 212.

For the intermediate drive member (which is also the cam member drive member) 250 the corresponding releasable coupling arrangement 300 comprises a reduced diameter rearward section 340. The rearward section 340 has a generally annular profile with a reduced external diameter in comparison to the main body 345 of the intermediate drive member 250. The rearward section is radially segmented to define a plurality of flexible finger portions 344 which extend rearwardly from the body main body 345. Each flexible finger portion 344 is provided with an inwardly radially directed tab or projection 342. The projections 342 are shaped and configured to compliment the recess 310 in the plunger 210.

It will be noted that both the projections 342 and recess 310 are provided with tapered edge profiles. This ensures that the releasable coupling arrangement 300 is easily released. In order to maintain the releasable coupling arrangement 300 in engagement a coupling member 350 is provided. The coupling member comprises a tubular collar with a radial flange 352. The rearward face of the flange 352 positions the coupling member against the forward surface of the rear transverse surface of the latch member 230. The forward face of the flange 352 provides a seat for the spring 220. As such, the coupling member 350 is captive between the latch 230 and the spring 220.

The coupling member 350 generally extends around the rearward section 340 of the intermediate drive member 250. The internal diameter of the coupling member 350 closely matches the external diameter of the rearward section 340. Thus, in the pre-firing position shown in the figures the flexible fingers 344 of the intermediate drive member 250 are blocked from deflect radially outwardly by the coupling member 350. As such it is not possible for the projections 342 to disengage the recess 310 of the plunger 210 when the releasable coupling 300 is axially aligned with the coupling member 350.

Figure 4:
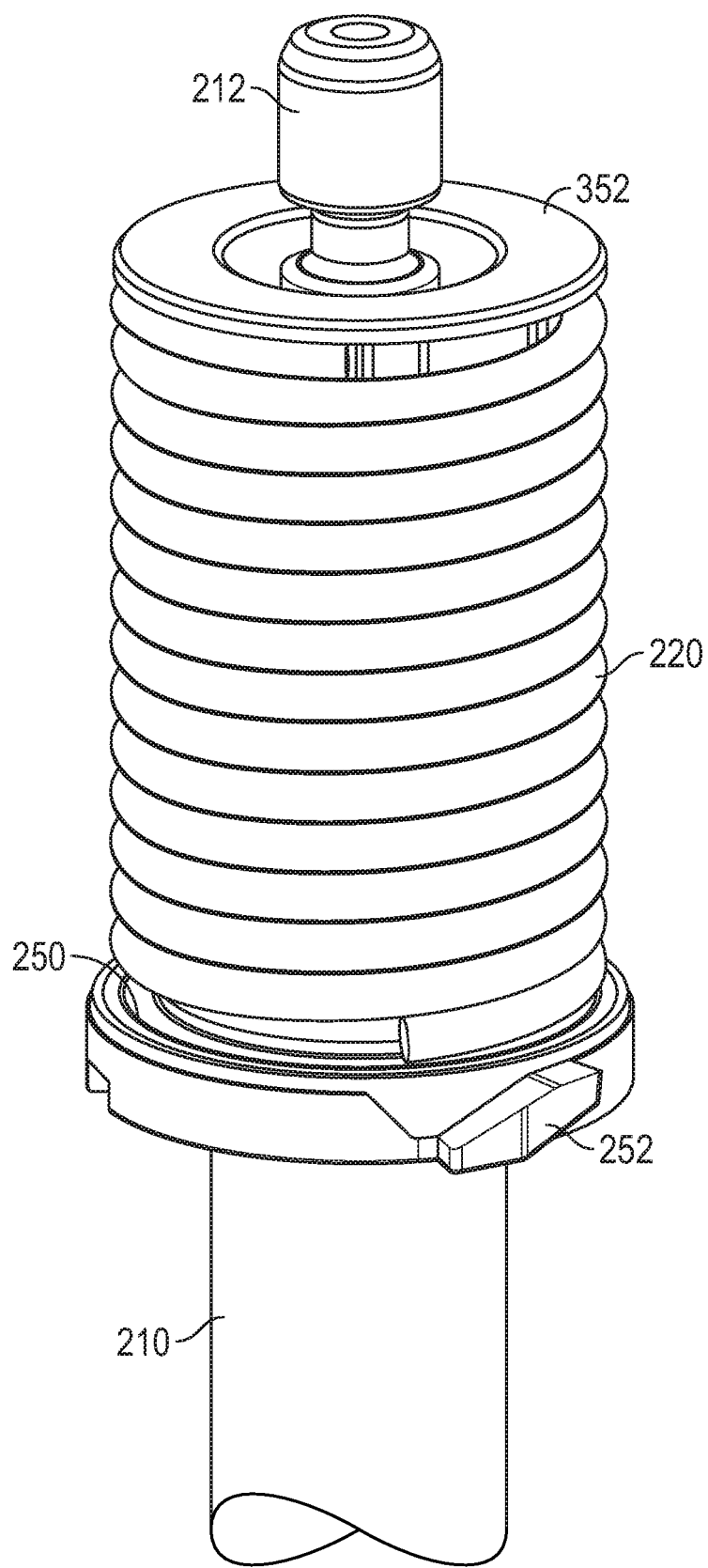
FIG. 4 shows an external three-dimensional view of the actuation mechanism of FIG. 2 in a pre-fired state.

As best seen in FIG. 4, the forward end of the intermediate drive member 250 is provided with at least one cam element 252. For example the intermediate drive member may typically be provided with at least one pair of radially opposed cam elements 252 which extend outwardly from a flange positioned forwardly of the spring 220. A corresponding internal groove is provided on an inner surface of the latch member 230 and defines a cam surface 262 along which the cam element 252 will travel.

The actuation sequence of the mechanism 200 and velocity regulator will now be described. The pre-firing configuration of the actuation mechanism 200 is shown in the figures. In this configuration the head 212 of the plunger 210 is retained in the aperture of the latch 230. As such both the first compression spring 220 and the second compression spring 222 are in a compressed, energised, state.

The user activates the device by urging the trigger button 40 forwards. The trigger button 40 acts upon the latch 230 and/or the head 212 of the plunger 210 to enable the plunger 210 to pass through the latch aperture. This releases the actuation mechanism to move the plunger 210 forwardly within the injection device (in the direction of arrow A).

The initial forward movement causes the cam members 252 to travel along the inclined path of the cam surface 262. As the first spring 220 expands its axial force is transmitted by the intermediate drive member 250 through the fully compressed second compression spring 222 to the forward end of the plunger 210. However, initially the plunger 210 is unable to travel beyond the intermediate drive member 250 as the releasable coupling 300 is prevented from releasing by the blocking action of the coupling member 350. It will be appreciated that due to the circumferential nature of the recess 310, it will be noted that the intermediate drive member 250 may freely rotate relative to the plunger whist maintaining the axial coupling.

Once the outer spring 220 has moved the intermediate drive member 250 (and therefore the coupled plunger 210) sufficiently forward relative to the latch 230 (which is axially fixed within the injection device), the releasable coupling 300 will move clear of the coupling member 350. With the coupling member 350 no longer restraining the flexible fingers 342 may deflect outwardly to allow the projections 342 to release the recess 310 of the plunger 210. In this (transient) configuration, the springs 220 and 222 are both acting to urge the plunger 210 away from the latch 230 and the inner spring 222 will force the plunger 210 to move forward beyond the intermediate member. As such the releasable coupling 300 will be released.

The release of the releasable coupling 300 will generally be sequenced to occur around the same time as the cam members 252 of the intermediate drive member 250 reach the end of the cam surface 262. In an autoinjector device this may be sequenced to occur at or close to the point at which the needle insertion has taken place (and the syringe is no longer moving relative to the injection device). As such, the velocity control arrangement may only be active during the needle insertion phase (and may limit the insertion of the needle to a desirable rate or reduce the risk of syringe breakage when the syringe movement is arrested). For the subsequent phase of activation (the "dose delivery" stage) the full force of both springs 220 and 222 may be available to urge the plunger 210 forward. This may be particularly beneficial for high viscosity drugs.

Figure 5:
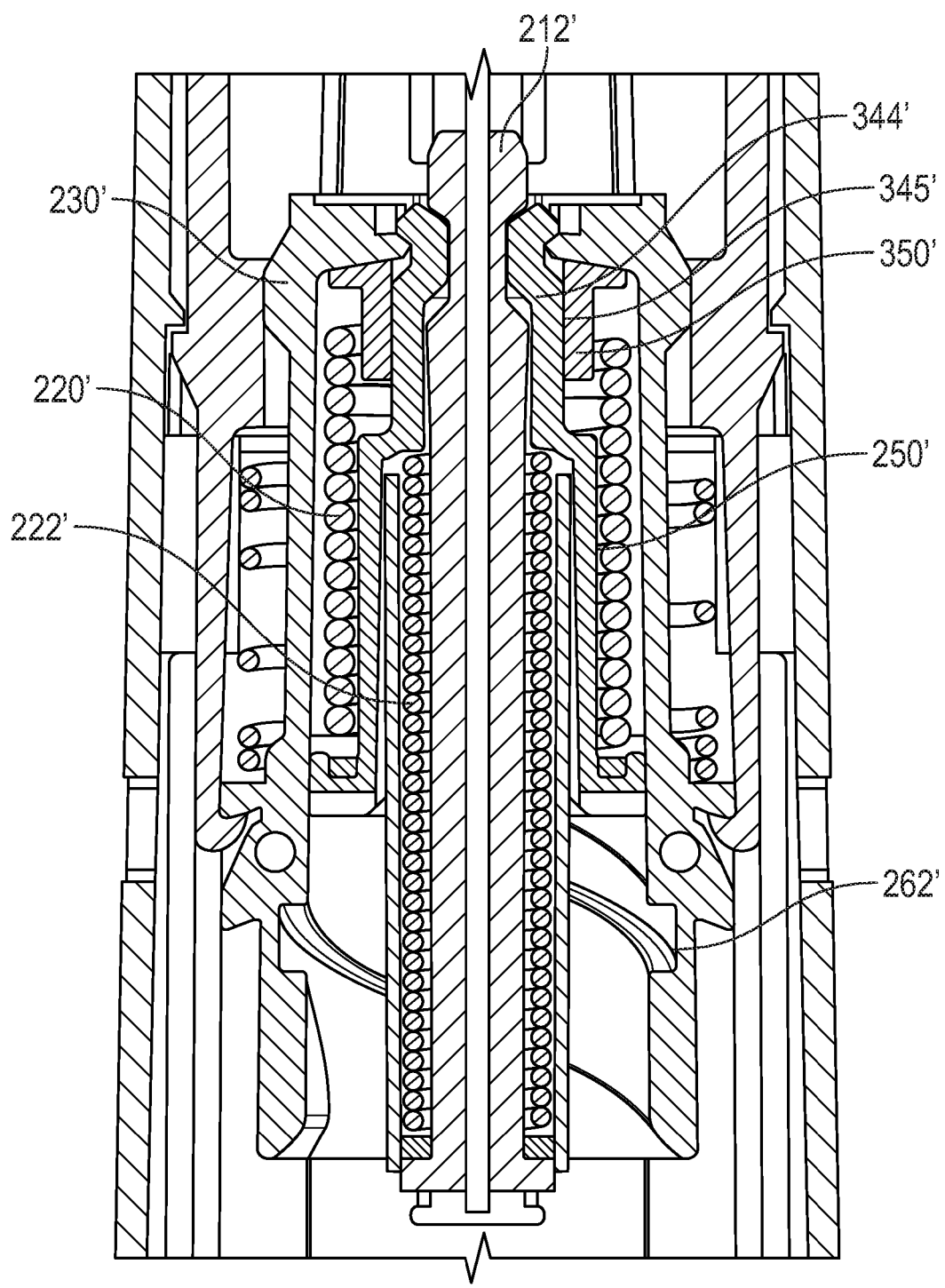
FIG. 5 shows a cross sectional side view of the actuation mechanism of an alternate embodiment.
Figure 6:
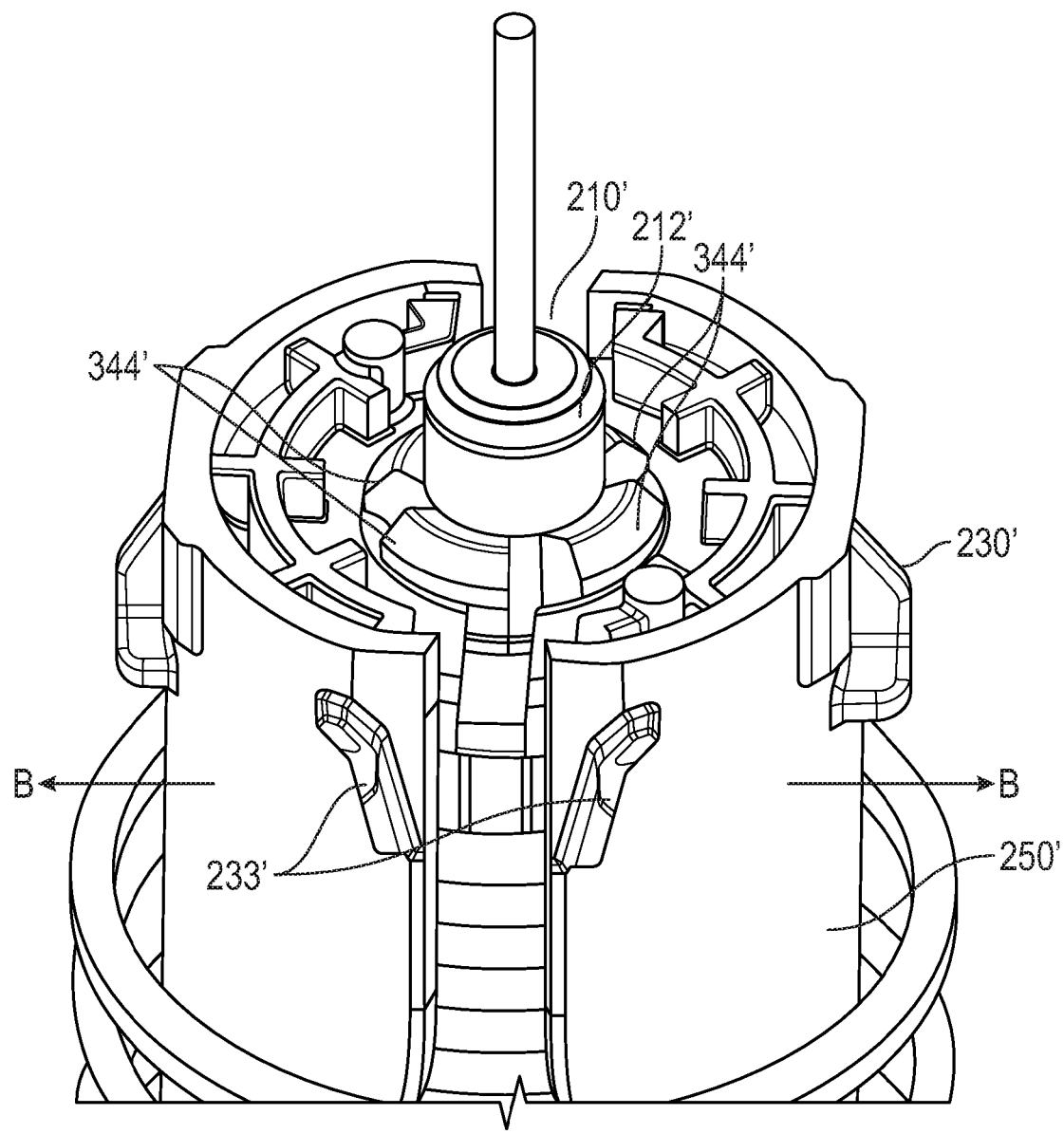
FIG. 6 shows a three-dimensional view of the actuation mechanism of FIG. 5 in a pre-fired state (and with the housing omitted for clarity).

An alternative embodiment of the invention is shown in FIGS. 5 and 6. In this embodiment the latching arrangement between the plunger 210', releasable coupling 300' and the latch 230' has been modified but the underlying operation of the invention is substantially unchanged. In contrast to the preceding embodiments, the enlarged head 212' of the plunger 210' of this embodiment is not directly engaged by the latch 230'; rather, the latch 230' engages and holds the outer surface of the rearward necked portion 344' of the releasable coupling 300'. Accordingly, the outer surface 345' may be provided with a suitable grooved or lipped profile to engage the latch 230'. The head of the plunger 212' is in turn held by the releasable coupling 300'. As in the previous embodiment the releasable coupling 300' is formed as part of an intermediate drive member 250' (disposed between the two drive springs 220', 222') and carries the cam members 252 of the velocity control arrangement on a forward, and outward, portion thereof. Thus, initially both the plunger 210' and releasable coupling 300' is held relative to the latch 230' against the forward biasing force of the drive springs 220' and 222'.

In use, the trigger 40' is urged forward relative to the latch 230' by the user. This movement causes internal features of the trigger 40' to engage and urge apart the surfaces 233' which are provided on opposing sides of the split formed in the rear body portion 232' of the latch 230'. This forces the portions to splay outwardly (in the direction shown by arrow B) so as to expand the latch and allow the latch 230' to release the releasable coupling 300'.

This releases the plunger 210' for forward movement under the force of the first, outer drive spring 220'. The expansion of the aperture in the latch 230' is not sufficient to allow the releasable coupling 300' to initially release the plunger 210'. As the head of the plunger 212' and the rearward necked portion 344' pass forward through the latch 230' they remain coupled so do not move relative to one another. The initial forward movement brings the latch 130' into alignment with the coupling member 350'. Thus the releasable coupling 300' must remain engaged with the plunger until the actuation movement has carried the plunger 210' forward sufficiently for the coupling to clear the forwardmost end of the releasable coupling 300'.

Thus, during the initial movement the engagement between the plunger 210' and coupling 300' cause the plunger to be fixed relative to the cam members (not shown). As such the cam members control/limit the initial velocity of the plunger in substantially the same manor as the previous embodiment. Once the plunger 210' passes further forward the flexible fingers 344' of the coupling 300' pass beyond the coupling member 350' and can splay outwardly to release the plunger from engagement with the intermediate drive member 250' and therefore disengage the velocity control arrangement.

An advantage of this embodiment is that it removes the need to accommodate for tolerances in the longitudinal direction between the plunger 210', latch 230' and the intermediate member 250'. Since all three components are actively engaged when the device is in the pre-fired configuration it is possible to avoid a delay between the release of the plunger and latch and full engagement between the plunger and intermediate member.

Although the invention has been described above with reference to a preferred embodiment, it will be appreciated that various changes or modifications may be made without departing from the scope of the invention as defined in the appended claims. For example, the skilled person will appreciate that the timing of the disengagement of the releasable coupling may depend on the particular configuration of the device. The skilled person will also appreciate that by varying the axial extent of the coupling member 350, embodiments of the invention may be readily tailored.

Whilst the illustrated embodiment includes two opposing cam surfaces the skilled person will appreciate that more or less features may be utilised in embodiments of the invention.

In the illustrated embodiment the cam surface defines a substantially constant threaded cam path but the skilled person will appreciate that the surface may have other sloped profiles (for example, a variable angle of incline) depending upon the velocity profile required for the forward movement of the plunger.

Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

Whilst the illustrated embodiment uses a coupling member which is a discrete component it will be appreciated that the function could equally be provided by a forwardly extending wall from the latch member. Further, whilst the illustrated embodiment forms the cam surface on an inner surface of the latch to allow for convenient manufacture, it will be appreciated that in other embodiments the surface could be formed by an integral feature of the housing or even by a discrete component fixed relative to the housing.

The invention claimed is:

1. An injection device for delivering a dose of medicament from a syringe, the injection device comprising:
   a housing;
   a plunger moveably mounted within the housing;
   an actuation mechanism arranged to provide a forward biasing force to urge the plunger forward in use in a delivery movement that expresses a dose of a medicament;
   a trigger mechanism arranged to releasably hold the plunger against the forward biasing force of the actuation mechanism; and
   a plunger velocity regulator comprising:
      a cam surface associated with the housing, and
      a cam member associated with the plunger and arranged to engage the cam surface during at least a portion of the delivery movement of the plunger such that axial movement of the plunger relative to the housing causes relative rotational movement of the cam member which limits a forward velocity of the plunger during the at least a portion of the delivery movement; and wherein
   the plunger is axially connected to the cam member by a releasable coupling comprising interconnecting engagement features on the plunger and the cam member,
      wherein the cam member comprises a resilient portion that causes release of the cam member from the plunger; and
   the plunger velocity regulator further comprises a coupling member which blocks release of the releasable coupling when the plunger is in a rearward position and wherein forward movement as part of the delivery movement of the plunger moves the releasable coupling out of engagement with the coupling member such that the plunger may disengage the cam member after the at least a portion of the delivery movement of the plunger.

2. The injection device of claim 1, wherein the actuation mechanism further includes:
   a first phase of operation in which the actuation mechanism displaces a syringe relative to the housing to automate an insertion of a needle into skin;
   a second phase of operation in which the plunger is displaced relative to the syringe to cause delivery of the medicament; and wherein
   the coupling member blocks release of the releasable coupling during the first phase of operation.

3. The injection device of claim 1, wherein the resilient portion of the cam member is deflectable to disengage the interconnecting engagement features to cause release of the cam member from the plunger.

4. The injection device of claim 3, wherein the coupling member blocks deflection of the resilient portion of the cam member until forward movement of the plunger moves the releasable coupling out of engagement with the coupling member.

5. The injection device of claim 3, wherein the resilient portion of the cam member comprises a plurality of resilient portions.

6. The injection device of claim 3, wherein the interconnecting enciaciement features of the releasable coupling comprise a plunger interconnecting feature comprising an annular groove or projection extending around an outer surface of the plunger and a cam member interconnecting feature comprising at least one projection or recess for engaging the annular groove or projection.

7. The injection device of claim 3, wherein the resilient portion of the cam member comprises a plurality of flexible members, each flexible member having a cam member interconnecting feature.

8. The injection device of claim 7, wherein the plurality of flexible members comprise a plurality of resilient segments formed in a reduced diameter rearward portion of the cam member.

9. The injection device of claim 1, wherein the coupling member comprises an annular collar.

10. The injection device of claim 9, wherein the coupling member comprises a seat for a drive spring of the actuation mechanism.

11. The injection device of claim 10, wherein the seat comprises a radial flange at a rearward end of the coupling member.

12. The injection device of claim 1, wherein the coupling member extends forwardly from a rearward surface associated with the trigger mechanism.

13. The injection device of claim 1, wherein the cam member is further configured as an intermediate drive member of the actuation mechanism, the actuation mechanism comprising a first drive spring disposed between the cam member and the housing, or a featured fixed relative to the housing, to urge a collar forward during actuation movement, and a second drive spring disposed between the cam member and the plunger to urge the plunger forward during activation movement.

14. The injection device of claim 13, wherein the first drive spring is released upon release of the plunger by the trigger mechanism and wherein the second drive spring is released when the plunger is axially disconnected from the cam member by the releasable coupling.

15. The injection device of claim 1, wherein the cam surface comprises an internal thread defined on an inner surface of the injection device.

16. An injection device for delivering a dose of medicament from a syringe, the injection device comprising:
a housing;
a plunger moveably mounted within the housing;
an actuation mechanism arranged to provide a forward biasing force to urge the plunger forward in use to express a dose of a medicament, the actuation mechanism comprising:
an intermediate drive member,
a first drive spring disposed between the intermediate drive member and the housing, or a feature fixed relative to the housing, to urge the intermediate drive member forward during actuation movement, and
a second drive spring disposed between the intermediate drive member and the plunger to urge the plunger forward during activation movement;
a trigger mechanism arranged to releasably hold the actuation mechanism when the injection device is in a pre-use configuration; and wherein
the trigger mechanism arrangement comprises a latch which releasably engages the intermediate drive member to hold the intermediate drive member in a rearward, pre-firing, position against the forward biasing force of the actuation mechanism; and
wherein the plunger is releasably coupled to the intermediate drive member by interconnecting engagement features on the plunger and the intermediate drive member such that the plunger and the intermediate drive member are axially fixed when the latch is holding the intermediate drive member, and
wherein the intermediate drive member comprises a resilient portion that causes release of the intermediate drive member from the plunger.

17. The injection device of claim 16, wherein the plunger is releasably coupled to the intermediate drive member for at least a portion actuation movement.

18. The injection device of claim 17, wherein the injection device further comprises a coupling member which blocks release of a releasable coupling when the plunger is in a rearward position and wherein forward movement of the plunger moves the releasable coupling out of engagement with the coupling member such that the plunger may disengage a cam member after an initial movement of the plunger.

* * * * *